US008101655B2

(12) United States Patent
Smith et al.

(10) Patent No.: US 8,101,655 B2
(45) Date of Patent: Jan. 24, 2012

(54) FLUORESCENT DYES AND COMPLEXES

(76) Inventors: Gerald Arthur Smith, Cambridge (GB); Darren William Watson, Norfolk (GB); Howard Paul Voorheis, Rathmines (IE)

( * ) Notice: Subject to any disclaimer, the term of this patent is extended or adjusted under 35 U.S.C. 154(b) by 0 days.

(21) Appl. No.: 12/694,510

(22) Filed: Jan. 27, 2010

(65) Prior Publication Data

US 2010/0256399 A1 Oct. 7, 2010

Related U.S. Application Data

(62) Division of application No. 10/599,767, filed as application No. PCT/GB2005/001325 on Apr. 6, 2005, now Pat. No. 7,674,918.

(30) Foreign Application Priority Data

Apr. 6, 2004 (GB) .................................. 0407836.6

(51) Int. Cl.
*A61K 31/35* (2006.01)
*C07D 311/88* (2006.01)
(52) U.S. Cl. ........................................ 514/454; 549/227
(58) Field of Classification Search .................. 549/227; 514/454
See application file for complete search history.

(56) References Cited

U.S. PATENT DOCUMENTS

| 2,219,009 A | 10/1940 | Wilhelm et al. |
| 6,130,101 A | 10/2000 | Mao et al. |

FOREIGN PATENT DOCUMENTS

| EP | 0314480 A | 5/1989 |
| EP | 0357350 A | 3/1990 |
| EP | 05733168 | 10/2010 |
| WO | WO 2005/098437 A3 | 10/2005 |

OTHER PUBLICATIONS

Avakyan, A. B. et al., "Use of Rhodamine 6G as a Fluorescent Probe for Investigating Chloroplast Membranes". Biophysics UK, vol. 29, No. 6, pp. 1069-1073 (1984).

Baraka, Mohamed E. et al., "Fluorimetric Studies of Solutions of Pyronin Dyes: Equilibrium Constants in Water and Partition Coefficients in Organic-Solvent Water Systems", Journal of Photochemistry and Photobiology A: Chemistry, vol. 56, pp. 295-311 (1991).

Fujiki, et al., "Spectral Studies of the Aqueous Solution of Pyronine G", Bulletin of the Chemical Society of Japan, vol. 35, No. 2, pp. 185-193 (1962).

McNamara, K. P. et al., "Synthesis, Characterization, and Application of Fluorescent Lipobeads for imaging and Sensing in Single Cells", Database Accession No. 6686157 and Proceedings of the SPIE—The Institution of Electrical Engineers, vol. 3922, pp. 147-157 (2000).

Ritucci, N. A. et al., "A Fluorescence Technique to Measure Intracellular pH of Single Neurons in Brainstem Slices", Journal of Neuroscience Methods, vol. 68, No. 2, pp. 149-163 (1996).

*Primary Examiner* — Taofiq A Solola

(57) ABSTRACT

A fluorescent dye comprising a xanthene-derived fluorophore having the formula (I) wherein $R^1$, $R^2$, $R^3$, $R^4$, $R^5$ and $R^6$ are independently selected from H, alkyl, alkoxy, alcohol, ether, alkenyl, alkenoxy, aryl, aralkyl and amido, except that $R^1$, $R^4$ and/or $R^5$ is not H when bonded to Y, $Y^1$ or $Y^2$, respectively; X is either $O^-$ or $S^-$; and at least one of Y, $Y^1$, $Y^2$, $Y^3$, $Y^4$ and $Y^5$ is a group for covalently bonding the dye, optionally through, the use of a coupling agent, to a target molecule, and is otherwise H. The dye may be covalently attached to a target molecule to form a complex, and the dye and/or complex finds use in cell analysis techniques, particularly pH measurement and analysis of kinetics of migration.

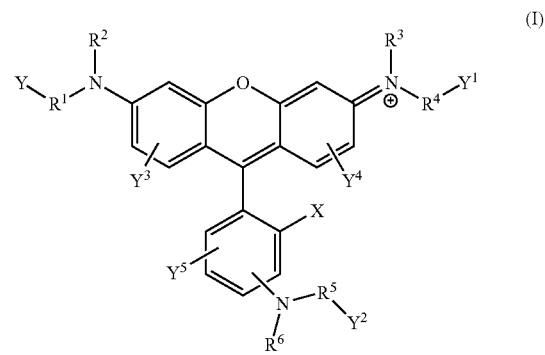

(I)

30 Claims, 2 Drawing Sheets

Image taken with green light

Image taken with red light

Sum of red and green images

Difference of red and green images

FLUORESCENT DYES AND COMPLEXES

CROSS-REFERENCE TO RELATED APPLICATIONS

This application is a divisional of U.S. application Ser. No. 10/599,767, filed Oct. 6, 2006, now U.S. Pat. No. 7,674,918 which was filed under 35 U.S.C. §371, and claims priority to International Application No. PCT/GB2005/001325, filed Apr. 6, 2005, which claims priority to Great Britain Application No. 0407836.6, filed Apr. 6, 2004, all of which are incorporated herein by reference in their entirety.

FIELD OF THE INVENTION

This invention relates to fluorescent dyes comprising a xanthene derived fluorophore, methods of making the same, complexes comprising these dyes, and use of such dyes and complexes in cell analysis procedures.

BACKGROUND OF THE INVENTION

Fluorescent dyes, when bonded to target molecules such as proteins, are commonly used to probe the properties of living cells. In particular, such dyes are often used to probe the pH of individual cell compartments. This is commonly achieved by comparing the intensity of fluorescence of a particular dye when it is within a particular cell compartment with a calibration curve of intensity versus pH for that dye.

In some instances, for example when greater accuracy is required, two dyes (with greatly different responses at the measured pH) are used. The ratio of the two observed intensities is compared to a calibration curve, to determine a pH value more reliably.

It has now been realised that even greater accuracy can be achieved by tailoring the most sensitive region of a dye's pH response to the expected pH of the cell or cell compartment. This can be done by using a dye whose $pK_a$ is approximately equal to the expected pH of the cell or cell compartment.

At present, long wavelength, fluorescent dyes bonded to suitable target proteins have $pK_a$'s of about 6 and above. However, some cell compartments of interest have a pH of less than 6. It would therefore be desirable to provide dyes which have $pK_a$'s of less than 6 when bound to protein, thus allowing their $pK_a$ to be matched to the approximate pH of their target cell compartment.

SUMMARY OF THE INVENTION

According to a first embodiment of the present invention, a fluorescent dye comprises a xanthene-derived fluorophore having the formula (I)

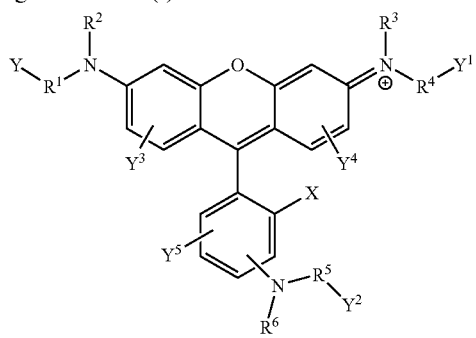

(I)

wherein $R^1$, $R^2$, $R^3$, $R^4$, $R^5$ and $R^6$ are independently selected from H, alkyl, alkoxy, alcohol, ether, alkenyl, alkenoxy, aryl, alkaryl, aralkyl and amide, except that $R^1$, $R^4$ and/or $R^5$ is not H when bonded to Y, $Y^1$, and/or $Y^2$, respectively;

X is either $O^-$ or $S^-$; and at least one of Y, $Y^1$, $Y^2$, $Y^3$, $Y^4$ and $Y^5$ is a group for: covalently bonding the dye, optionally through the use of a coupling agent, to a target molecule, and is otherwise H.

According to a second embodiment of the present invention, a method for making a dye of the type defined above comprises reacting a meta-aminophenol with a carboxylate compound capable of undergoing alpha-cleavage, e.g. a beta-ketocarboxylate.

According to a third embodiment of the present invention, a method for making a dye having the formula (I) defined above comprises reacting a compound having the formula (II)

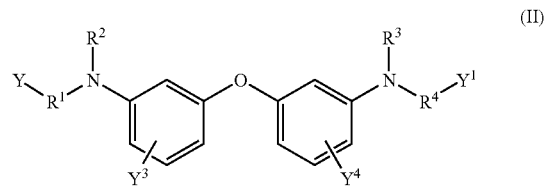

(II)

with a compound of formula $(CO)R^7_2$, wherein $R^7$ is a leaving group, to form an intermediate having the formula (III)

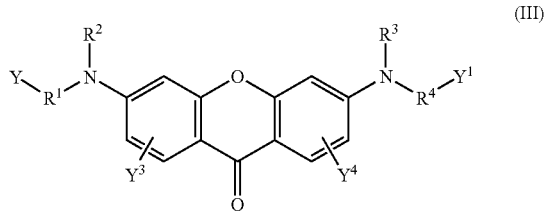

(III)

wherein $R^1$, $R^2$, $R^3$, $R^4$ and Y are as defined for formula (I), and converting the intermediate to a dye having the formula (I).

According to a fourth embodiment of the present invention, a method for making a dye having the formula (I) as defined above comprises reacting a compound having the formula (II), above, with a benzaldehyde, benzoic acid, activated benzoic acid or benzoate, wherein when reaction is with a benzaldehyde the method further comprises post-condensation oxidation to form a dye having the formula (I).

According to a fifth embodiment of the present invention, a method for making a dye having the formula (I) as defined above comprises reacting together a pare-amino substituted salicylaldehyde and a meta-aminophenol to form a compound having the formula (IIa), wherein $R^8$ is H or an alkyl group; cyclising the compound of formula (IIa) to form a compound having the formula (IIb); reacting the compound having the formula (IIb) with a meta-aminophenol to form a dye having the formula (IIc); and oxidizing the compound having the formula (IIc) to form a dye having the formula (I).

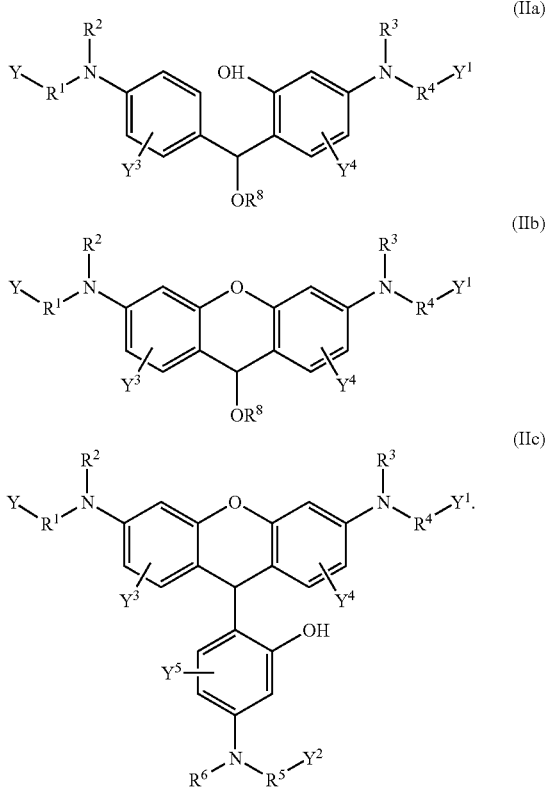

According to a sixth embodiment of the present invention, a method for making a dye having the formula (I) as defined above comprises reacting together a para-amino substituted salicylaldehyde and a meta-aminophenol in aqueous or alcoholic solution and in the presence of acid, to form a compound having the formula (IIa), above; cyclising the compound having the formula (IIa) to form a compound having the formula (IIb), above; converting the compound having the formula (IIb) to a compound having the formula (III), above; and converting the compound having the formula (III) to a dye having the formula (I).

According to a seventh embodiment of the present invention, a method for making a dye having the formula (I) as defined above comprises reacting together a meta-aminophenol with a compound having the formula

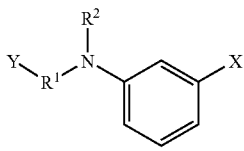

wherein X is a halogen, a $B(OR^9)_2$ group in which $R^9$ is H or an alkyl group, or another leaving group, to form a compound having the formula (II), above, and converting the compound having the formula (II) to a dye having the formula (I) by:

a) reaction with a salicylic ester;
 b) reaction with a salicylaldehyde, and subsequent oxidation; or
 c) converting to a compound having the formula (II), above, and then converting this to a dye having the formula (I).

According to an eighth embodiment of the present invention, a fluorescent complex comprises a dye having the formula (I) as defined above, which is bonded to a target molecule through a group selected from Y, $Y^1$, $Y^2$, $Y^3$, $Y^4$ and $Y^5$, which is not H. optionally through the use of a coupling agent.

The dyes and complexes of the present invention show a negative fluorescence intensity response with increasing pH. This means that the intensity of fluorescence exhibited by the dyes and complexes decreases with increasing (i.e. more alkaline) pH. Furthermore, the pals of these dyes and complexes may be varied by selection of the substituents $R^5$ and $R^6$, and by the inclusion of electron donating groups on the lowermost aryl ring, to give a range of dyes and complexes having $pK_a$'s particularly suited to cell analysis procedures.

According to a ninth embodiment of the present invention, a living cell or cell compartment comprises a complex as defined above, either bonded thereto or contained therein.

According to further embodiments of the present invention, such dyes and complexes are used, either alone or in combination with other dyes or complexes, to establish the pH of a living cell or cell compartment, or to analyse the kinetics of migration of the dyes or complexes into a living cell or cell compartment, or from location to location within a cell. Yet another embodiment of the invention comprises a novel method of making intermediates en route to the dyes of the present invention.

DETAILED DESCRIPTION OF THE INVENTION

Figure 1:
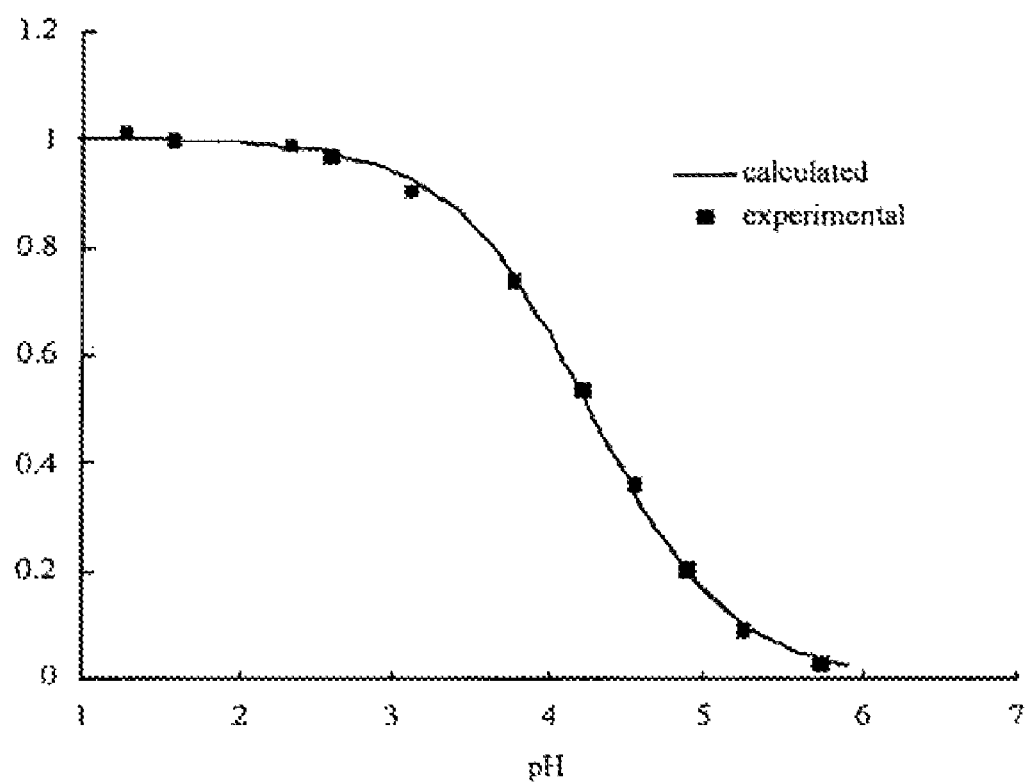
FIG. 1. Fluorescence titration of a dye having the formula (VII).

Dyes according to the present invention are based on a rhodamine-type structure, and as such comprise a xanthene-derived fluorophore and an additional aryl ring. The xanthene derived fluorophore and the aryl ring are mutually perpendicular, and therefore no conjugation exists between them.

In formula (I), the groups $R^1$, $R^2$, $R^3$ and $R^4$ on the xanthene moiety are independently selected from H (except that $R^1$ and/or $R^4$ can not be H if Y or $Y^1$ is bonded thereto, respectively), alkyl, alkoxy, alcohol, ether, alkenyl, alkenoxy, aryl, alkaryl, aralkyl and amide. The size of these groups is limited only by steric considerations, and the need for compatibility with whichever method of coupling the dye to a target molecule is desired. Typically, however, these groups comprise up to 20 carbon atoms. Preferably, these groups are independently selected from alkyl groups, more preferably alkyl groups having up to 10 carbon atoms.

For clarity, in the context of the present application, reference to groups such as alkyl, alkoxy etc. include substituted and unsubstituted groups. Furthermore, any of the aryl rings may include additional substituents not shown in formula (I).

Where water solubility of the dye is required, for instance to allow bonding to a protein without denaturation of the protein, one or more of $R^1$, $R^2$, $R^3$ and $R^4$ are selected from or include polar groups such as alcohol, alkoxy, ether, amido, carboxylate, sulphonate, amino, ammonium etc.

The aryl ring of the dye bears two substituents, X and $NR^5R^6$. The X group is ortho to the xanthene moiety, and is believed responsible for the pH response of the dye. X may be selected from O⁻ and S⁻, but is preferably O⁻. The protonated forms of the group X, ie. OH and SH, are also encompassed by the present invention.

The $NR^5R^6$ substituent can take any available position on the phenyl ring, although preferably it is pare to the xanthene moiety. $R^5$ and $R^6$ are independently selected from H (unless y1 is bonded to $R^5$, alkyl, alkoxy, alcohol, ether, alkenyl, alkenoxy, aryl, alkaryl or aralkyl or amide. More preferably, however, $R^5$ and $R^6$ are independently selected from alkyl, alcohol or ether groups, and are most preferably alkyl groups.

As for groups $R^1$ to $R^4$, the size of groups $R^5$ and $R^6$ is limited only by steric considerations, and the need for compatibility with whichever method of coupling the dye to a target molecule is desired. Typically, however, these groups comprise up to 20 carbon atoms, and more typically up to 10 carbon atoms.

A particularly preferred dye comprises X as ° (or OH) and each of $R^1, R^2, R^3, R^4, R^5$ and $R^6$ independently selected from alkyl groups.

Optionally, the aryl ring may comprise one or more additional substituents which may occupy any available position on the ring. It is preferred that such substituents are electron donating in nature, unless the substituent is for bonding to a target molecule, as is described below. Alkyl groups, typically having from 1 to 10 carbon atoms, are preferred electron donating substituents.

The dyes are functionalised so that they may be bonded to a range of target molecules, for introduction into a living cell or cell compartment. If desired, a plurality of different dyes, having fluorescence responses at different plus, may be bonded to a single target molecule. This may be particularly useful for analysing the kinetics of migration of a particular target molecule through different regions of a cell, or through different cell compartments.

In the context of the present Application, a living cell includes eukaryotic cells, prokaryotic cells and plant cells. Further, while the present invention is described in the context of use of the novel fluorescent dyes with living cells, the present invention may find use in other applications, and in particular in the analysis of non-biological systems.

Suitable target molecules include peptides, polypeptides, proteins, sugars (i.e. saccharides and polysaccharides) and antibodies.

There is a wide variety of functionalities that may be included in the dyes of the present invention to achieve bonding to target molecules. For clarity, bonding may be achieved by direct reaction between a dye and its target S molecule, herein referred to as "direct bonding". Alternatively, "indirect bonding" may be achieved with the aid of a coupling agent, or "activator", which activates the dye by forming a complex therewith, and which is typically displaced after reaction with the target molecule. Depending on the nature of the coupling agent, however, a moiety derived therefrom may become incorporated in the final bonded complex. A wide variety of coupling reactions is known in the prior art, and may be applicable to the present invention.

Bonding to a target molecule may take place through any i one of groups $Y, Y^1, Y^2, Y^3, Y^4$ or $Y^5$, when these are not H. and which hereinafter are referred to collectively as the "bonding groups". A single dye may contain more than one bonding group suitable for bonding to a target molecule, but generally bonding only occurs through one of these groups.

Generally, it is preferred that the dye be bonded to a target molecule through a substituent on the xanthene moiety, i.e. $Y, Y^1, Y^3$ or $Y^4$, rather than through $Y^2$ or $Y^5$ as the substituent —$NR^5R^6$ is believed to affect the pea of the dye or complex, as will be described in more detail below, and other substituents on the same aryl ring may have a similar effect.

Generally, if bonding to a target molecule is to be achieved through either of groups $Y^3$ or $Y^4$, steric considerations need to be taken into account. Typically group $Y^3$ and/or $Y^4$ will be ortho or meta, preferably ortho, to the nitrogen-containing group, $NR^1R^2$ or $NR^3R^4$. If bonding is to be achieved through a group located mete to this group it is preferred that bonding should not be via a hetero atom, as this may reduce or remove the fluorescence response.

The nature of the bonding group, or groups, will depend upon the nature of the functional groups on the target molecule available for reaction with the dye. For instance, where the target molecule contains pendant amino or amine groups, the bonding group may be selected from isocyanates; isothiocyanates; and carbonyl groups containing a leaving group, for instance acid chloride, sulphonate, carboxylate, and so-called 'active" esters, i.e. containing very good leaving groups including, for instance, nitrophenyl and N— hydroxysuccinimide, all of which are capable of direct bonding to said amino or amine groups on the target molecule. Alternatively, the bonding group may comprise a carboxylic acid group, an aldehyde or a ketone which, on activation with a coupling agent, are capable of reaction with said amino or amine groups. When the bonding group is an aldehyde or ketone, the reaction is typically conducted under reducing conditions to give rise to an amino-alkyl chain linkage in the final dye/target molecule complex.

Where the target molecule comprises a thiol group available for reaction with the dye, the bonding group may be selected from many of the groups mentioned above, disulphide and thiols.

For clarity, many of the above bonding groups will react with and bond to a wide variety of target functional groups on target molecules, i.e. other than amino, amine and thiol groups, optionally through the use of a coupling agent.

In case the bonding group is an additional substituent on one of the aryl rings of the xanthene moiety, preferred bonding groups include carboxylic acids, ethers and groups attached to the ring(s) through an alkyl group.

For cell analysis procedures, it is preferred that the dyes or complexes of the present invention have a range of $pK_a$'s in the range 1 to 7, more preferably 2 to 5.5. As mentioned above, the $pK_a$'s of these dyes appear to be primarily governed by the $R^5$ and $R^6$ substituents, and any additional substituents, on the aryl ring. For example, it seems that the pays of these dyes increase as $R^5$ and $R^6$ are progressed through primary to secondary to tertiary alkyl substituents. This finding is surprising, since, as discussed above, the aryl ring is not conjugated with the xanthene moiety. This lack of conjugation would be expected to minimise any effect of the $R^5$, $R^6$ and other substituents on the energy levels of the xanthene fluorophore, and hence minimize any changes to the fluorescence response of this fluorophore, consequently minimising any change in ply.

By way of illustration, Table 1, below, lists a number of dyes, some prior to functionalisation, and complexes according to the present invention (in each X is O⁻), together with their $pK_a$ values. In Table 1, and throughout the present application, Me denotes a methyl group, Et an ethyl group and Ph a phenyl group.

The dyes according to the present invention can be prepared by any combination of standard chemical synthetic steps. In the following, the syntheses described focus on the preparation of dyes in which the $NR^5R^6$ substituent is pare to the xanthene moiety, but may be modified if necessary by routine measures to prepare dyes having this substituent in other positions.

One method of preparation of the dyes of the present invention involves reaction of a meta-aminophenol (or a mixture of meta-aminophenols) with a carboxylate compound capable of undergoing alpha-cleavage, for instance a beta-ketocarboxylate. A preferred beta-ketocarboxylate is diethylmalonate. Another example of a carboxylate compound capable of undergoing alpha-cleavage suitable for use in the present invention is 5 nitrosalicylic acid methyl ester.

The reaction proceeds via an intermediate having the formula (III), below, wherein $R^1$, $R^2$, $R^3$, $R^4$ and Y are as defined for formula (I), which on further reaction with the carboxylate compound is converted to a dye having the formula (I).

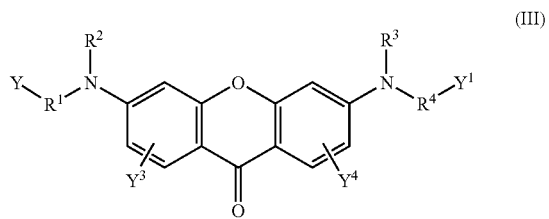

Another method of preparing the dyes according to the present invention comprises reacting a compound having the formula (II) above, with a compound of formula $COR^7{}_2$, wherein $R^7$ is a leaving group, to form an intermediate having the formula (III) above, and converting the intermediate to the desired dye by reaction with a meta-aminophenol (or a mixture of meta aminophenols), or a derivative thereof, or by standard chemical steps. One such combination of standard chemical steps comprises reducing the carbonyl group of the intermediate and turning the resulting OH group into a leaving group; condensing with a suitable molecule; and then reoxidising to a dye having the formula (I).

Yet another method for preparing the dyes of the present invention comprises reacting a compound having the formula (II), above, with a benzaldehyde, benzoic acid, activated benzoic acid, or benzoate. Where the method comprises reaction with a benzaldehyde the resulting product must be oxidised to produce a dye having the formula (I). In the context of the present Application, the term "activated benzoic acid" is intended to cover benzoic acid derivatives such as benzoic acid chlorides.

Yet another method for preparing the dyes of the present invention, which is particularly useful for preparing dyes in which the aryl rings of the xanthene moiety are different to one another, comprises reacting together a pare-amino substituted salicylaldehyde and a meta-aminophenol to form a compound having the formula (IIa), as shown above. The reaction is typically conducted in aqueous or alcoholic solution and in the presence of acid. Dilute acid may be used, —although stronger acids may avoid the need for heat to drive the reaction. Examples of suitable acids include hydrochloric acid and phosphoric acid. If the reaction takes place in an alcoholic solution this may result in $R^8$ being other than H. and typically it will be an alkyl group derived from the alcohol present. Any liquid alcohol may be used, with the lower ($C_{1-6}$) alcohols, such as methanol, ethanol, propanol and butanol, being preferred.

Alternatively, the salicylaldehyde might be replaced by a para-amino substituted ester of salicyclic acid.

The next step in this method requires cyclisation of the compound having the formula (IIa) to a compound having the formula (IIb), again as shown above. Cyclisation is typically acid catalysed. The compound having the formula (IIb) may then be reacted in a number of ways, either a) to form a compound having the formula (IIc), again as above, followed by oxidation to the desired dye of formula (I), or b) oxidation to a compound having the formula (III), with subsequent conversion I to the desired dye of formula (I). If, as is preferred, the reaction is to proceed via a compound having the formula (IIc), this requires reaction with further meta-aminophenol, selected according to the desired product. If the reaction is to proceed via a ketone of formula (III), this may be obtained from compound (IIb) using the methodology described by Ehrlich et al, Chem. Ber (1 913)4 6:194 1. Essentially, this involves substituting the group —ORB with chlorine, reacting with a cyanide salt to replace chlorine with a nitrite group, and oxidising to form a ketone.

Yet another method for preparing the dyes of the present invention, which is again suitable for preparing dyes in which the aryl groups of the xanthene moiety differ from one another, comprises reacting together a meta-aminophenol with a compound having the formula

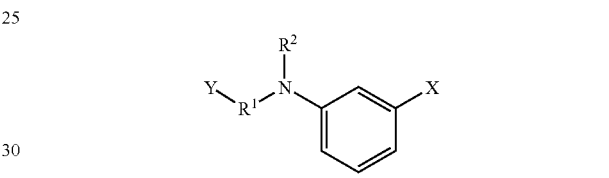

wherein X is a halogen, such as Cl, Br or I, a $B(OR^9)_2$ group in which 9 is H or an alkyl group, or another leaving group. The reaction is typically conducted in the presence of a base and a copper compound. Suitable copper compounds include the cuprous salts CuI, $Cu_2O$ and CuOAc (where Ac is acetate), and copper bronze. Platinum salts are also suitable for use in this reaction. Suitable bases include inorganic bases such as sodium or potassium carbonate, and organic bases such as di-isopropylethylamine (DIPE).

The resulting product, having the formula (II) above, may be converted to the desired dye by a) reaction with a salicylic ester; b) reaction with a salicylaldehyde having the formula (IIc), above, and subsequent oxidation; or c) converting to a I compound having the formula (III), above, and then to the desired dye.

Choice of reaction conditions and reagents for use in all these methods are well within the capability of the skilled practitioner.

The dyes and complexes of the present invention can be used to determine the pH of living cells or cell compartments. By "a cell compartment typically we mean one of the many organelles suspended in the cell cytoplasm. The pH of a cell or cell compartment can be measured by introducing a dye or complex into a cell or cell compartment, irradiating the dye or complex with a suitable light source, and observing the intensity of fluorescence of the dye or complex. The observed fluorescence intensity can then be used to determine pH by a variety of methods known in the field, selected according to the method of accumulation of the dye or complex. For instance, the observed fluorescence may be compared to a known standard, for example a calibration curve of fluorescence intensity versus pH, or to fluorescence intensity measurements indicative of the total dye or complex present. Any conventional fluorimetric equipment can be used to irradiate the sample, and to measure the resulting fluorescent response.

Typically, the dyes and complexes are introduced into a living cell or cell compartment by mixing with a sample comprising a cell or cell compartment, and then leaving the mixture to stand for a time interval adequate to allow entry of the dye or complex into the cell or cell compartment. During this time interval, the dye or complex diffuses towards a cell or cell compartment within the sample. The dye or complex then attaches itself to the membrane of a cell or cell compartment.

In the case of complexes, target molecules are generally cell or cell compartment specific, hence a specific complex generally attaches to only one kind of cell or cell compartment. Once attached to a cell or cell compartment, the dye or complex may diffuse through a membrane of that cell or cell compartment or be trafficked to a specific cell compartment by receptor-mediated endocytosis, hence exposing itself to the internal pH of the cell or cell compartment.

The dyes and complexes of the present invention allow more accurate determination of pH as compared to existing dyes because the $pK_a$'s of the dyes and complexes of the present invention can, by design, be adjusted by substitution to a variety of $pK_a$ values. Thus, some are tuned to the pH of the cell or cell compartment of interest, and consequently will be ideal for measuring the pH of a cell or cell compartment when accumulated by receptor-mediated endocytosis or any non-passive accumulation mechanism. Others will have a pea far from the pH of the cell or cell compartment of interest, and will be ideal for measuring pH when accumulation occurs by passive accumulation. This situation is best understood by considering these two mechanisms of accumulation of the dye or complex into the cell or cell compartment.

First, if the dye or complex is accumulated only passively according to the pH difference between the pH of the cell or cell compartment to be investigated and the pH outside the cell or cell compartment, respectively, then the accuracy of pH measurement with a dye or complex is highest when the $pK_a$ of the dye or complex is far from the pH to be measured. In this situation one is essentially measuring the accumulation at equilibrium as reported by fluorescence. Accumulation will occur passively when one form of the dye or complex with respect to pH (the uncharged form) freely penetrates the cell or cell compartment of interest and the other form (a charged form) is non-penetrating. Fluorescence will approach its equilibrium position provided the form of the dye accumulated is the fluorescent form and that accumulation to equilibrium has occurred. The observed fluorescence intensity can then be used to determine pH according to any of the known methods, for instance by reference to callibration data, or by comparing the observed fluorescence intensity to the fluorescence intensity observed on acidifying the test sample so that all the dye or complex fluoresces, the ratio of the two fluorescence intensities coupled with the known $pK_a$ allowing determination of pH. Passive accumulation can be achieved by use of a dye that is not attached to a target molecule or a dye that is attached to a small, relatively hydrophobic target molecule capable of diffusing through the cell membrane.

Second, whenever the dye or complex is accumulated in the cell or cell compartment by a mechanism that does not rely solely on passive accumulation, the accuracy of a pH measurement will be highest when the $pK_a$ of the dye is close to the pH to be measured. The increased accuracy available with the dyes and complexes of the invention in this situation arises from the fact that the $pK_a$ is the pH of the aqueous medium containing a species when it is 50% protonated and that at this pH a change in proton intensity will have greatest effect on the properties of the species. Hence, the greatest change in fluorescence intensity occurs at the $pK_a$ of the dye, and measurements of absolute fluorescence intensity at this pH will give rise to more accurate pH readings. That said, provided the titration range of the dye or complex used to analyse a particular cell or cell compartment embraces the pH of that cell or cell compartment, that is generally sufficient.

In the context of the present Application, a $pK_a$ is "far" from the pH to be measured when different by more than 1 pH unit, and preferably more than 2 pH units. For instance, if the dye or complex is a weak acid its $pK_a$ should be more than 1 pH unit below the pH to be measured, and if the dye or complex is a weak base then its $pK_a$ should be more than 1 pH unit above the pH to be measured. Further, in the context of the present application, a $pK_a$ is "close to the pH to be measured when they are within about 1 pH unit of each other.

Accuracy can be further increased by using a plurality of fluorescent dyes or complexes having different fluorescent responses. For instance, two or more dyes according to the invention may be used, optionally bonded to identical target molecules, or a dye according to the invention and another dye.

In one embodiment, the second fluorescent dye or complex has a positive fluorescence response with increasing pH (by this we mean that the intensity of fluorescence exhibited by the dye or complex increases with increasing pH). It is preferable that the two or more dyes or complexes have overlapping titration ranges, and more preferably the different dyes or complexes have $pK_a$ values within about 1 unit of each other. The intensity of fluorescence of each dye or complex is then measured, and pH determined by calculating the ratio:

$$\frac{\text{fluorescence intensity of the first dye or complex}}{\text{fluorescence intensity of the second dye or complex}}$$

and comparing the value obtained to a calibration curve.

According to another embodiment of the present invention, the dyes or complexes of the invention can be used to analyse the kinetics of migration of a species into or through a cell or cell compartment. This is done by monitoring the intensity of fluorescence of a dye or complex over a time interval. Where pH is known, the dye or complex should be selected so as to have a $pK_a$ in the range between the pH at the starting point and the pH at the end point of the pathway to be analysed. In some cases it may be desirable to use a plurality of dyes or complexes having a variety of $pK_a$'s, with each dye or complex tuned to a different portion of the pathway to be analysed.

According to yet another embodiment of the present invention, novel dyes are defined by formula (IV), below, wherein $R^1$, $R^2$, $R^3$, $R^4$, $R^5$ and $R^6$ are independently selected from H, alkyl, alkoxy, alcohol, ether, alkenyl, alkenoxy, aryl, alkaryl, aralkyl and amide; and X is either $O^-$ or $S^-$; with the proviso that when X is $O^-$, and preferably irrespective of the nature of X, not all of $R^1$, $R^2$, $R^3$, $R^4$, $R^5$ and $R^6$ are the same alkyl group, unless an electron withdrawing group is present in the aryl ring having the —$NR^5R^6$ group, eg. para to the group X.

According to yet another embodiment, when X is $O^-$ in formula (IV), not all of $R^1$, $R^2$, $R^3$, $R^4$, $R^5$ and $R^6$ are alkyl.

The preferred definitions of the various substituents are as for the dyes of formula (I) above, and additional substituents may be included on any of the aryl rings. A preferred substituent is pare to the group X (which is preferably $O^-$) and is selected from electron donating groups, for instance alkyl groups, typically $C_{1-6}$ alkyl groups.

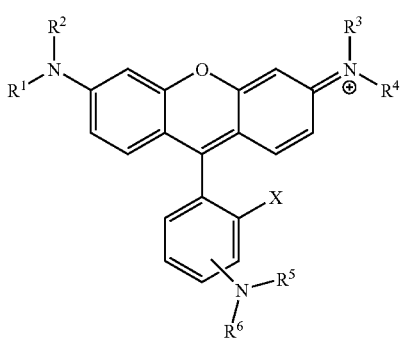

(IV)

The dyes of formula (IV) may be prepared by any of the methods described above for preparation of the dyes having the formula (I). Furthermore, these methods my be used for the preparation of dyes having the formula (IV) even when X is $O^-$ and each of $R^1$, $R^2$, $R^3$, $R^4$, $R^5$ and $R^6$ are the same or different alkyl groups.

The dyes of formula (IV) may be functionalised by standard chemical steps to give dyes having the formula (I) above, and may then be bonded to target molecules for cell analysis procedures.

and (VII) were prepared as shown in Scheme 1 and Scheme 2, respectively, below. The remaining starting materials were prepared by standard chemical syntheses.

Scheme 1

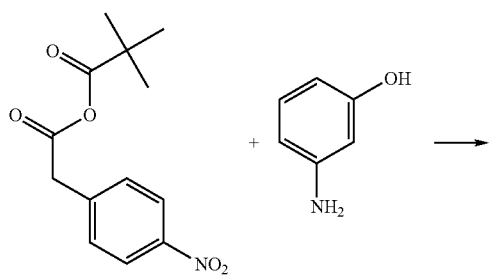

(V)

TABLE 1

| $R^1$—Y | TARGET MOLECULE | $R^2$ | $R^3$ | $R^4$ | $R^5$—$Y^2$ | $R^6$ | $pK_a$ |
|---|---|---|---|---|---|---|---|
| DYES | | | | | | | |
| Me | — | Me | Me | Me | Me | Me | 3.5 |
| Et | — | Et | Et | Et | Et | Et | 4.5 |
| Me | — | Me | Me | Me | $HOCH_2CH_2$ | $HOCH_2CH_2$ | 2.4 |
| $HOCH_2CH_2$ | — | $HOCH_2CH_2$ | $HOCH_2CH_2$ | $HOCH_2CH_2$ | $HOCH_2CH_2$ | $HOCH_2CH_2$ | 2.3 |
| Me | — | Me | Me | Me | $NO_2PhCH_2CH_2$ | Et | 2.7 |
| $NH_2C_6H_4CH_2CH_2$ | — | Et | Me | Me | Et | Et | 3.9 |
| $NH_2PhCH_2CH_2$ | — | Et | Et | Et | Et | Et | 4.4 |
| $Me(OCH_2CH_2)_2$ | | $Me(OCH_2CH_2)_2$ | $Me(OCH_2CH_2)_2$ | $Me(OCH_2CH_2)_2$ | $Me(OCH_2CH_2)_2$ | $Me(OCH_2CH_2)_2$ | 2.3 |
| $NH_2C_6H_4CH_2CH_2$ | | Et | $Me(OCH_2CH_2)_2$ | $Me(OCH_2CH_2)_2$ | $Me(OCH_2CH_2)_2$ | $Me(OCH_2CH_2)_2$ | 2.4 |
| $Me(OCH_2CH_2)_2$ | | $Me(OCH_2CH_2)_2$ | $Me(OCH_2CH_2)_2$ | $Me(OCH_2CH_2)_2$ | $NH_2C_6H_4CH_2CH_2$ | Et | 2.7 |
| $NH_2C_6H_4CH_2CH_2$ | | Et | $Me(OCH_2CH_2)_2$ | $Me(OCH_2CH_2)_2$ | Et | Et | 4.3 |
| COMPLEXES | | | | | | | |
| $NHCSNC_6H_4CH_2CH_2$ | Dextran | Et | Me | Me | Et | Et | 3.9 |
| $NHCSNC_6H_4CH_2CH_2$ | transferin | Et | Me | Me | Et | Et | 2.0 |
| Me | Dextran | Me | Me | Me | $NHCSNC_6H_4CH_2CH_2$ | Et | 2.9 |
| $NHCSNC_6H_4CH_2CH_2$ | transferin | Et | Me | Me | Et | Et | 2.0 |
| $NH_2C_6H_4CH_2CH_2$ | BSA | Et | $Me(OCH_2CH_2)_2$ | $Me(OCH_2CH_2)_2$ | Et | Et | 2.2 |

The present invention is now illustrated by the following examples.

EXAMPLES

A variety of different dyes according to the present invention were prepared as follows:

Example 1

Preparation of Starting Materials

Starting materials for the preparation of dyes according to the present invention and having the formulae (V) and (VI)

-continued

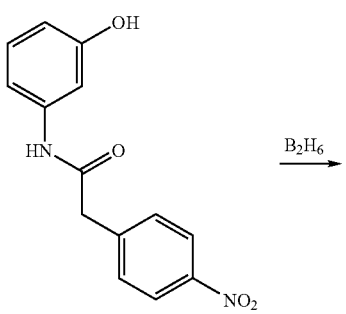

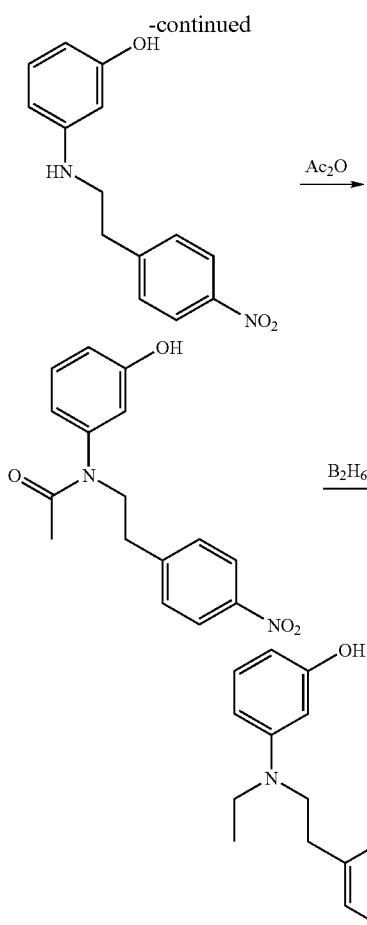

1a) N-(3-hydroxy-phenyl)-2-(4-nitrophenyl)-acetamide

Pyridine (14 g, 0.18 Mol) and 4-nitrophenylacetic acid (32 g, 0.18 Mol) were stirred in toluene (100 ml) whilst trimethylacetylchloride (21 g, 0.18 Mol) was added. The toluene was evaporated to yield 4-nitrophenylacetic trimethylacetic anhydride. 3-Aminophenol (20 g, 0.18 Mol) was stirred in DMF (100 ml) and treated with the mixed anhydride and pyridine (14 g) in dimethylformamide (DMF) dropwise. The solution was diluted with water and the product isolated by filtration and dried (19 g, 39%).

1b) N-2(4-nitrophenyl)ethyl-N-(3-hydroxyphenyl)-acetamide 10 g (0.4 mol) of the nitrophenylacetanilide prepared in 1a) was placed in a flask and borane in tetrahydrofuran (THF) (1 M, 250 ml) was added carefully. The resulting solution was heated under reflux and water (12 ml) in THF (100 ml) was added dropwise over 1 hour. A further 50 ml of water was added and the mixture was heated for 15 mins. The THF was evaporated under reduced pressure and methanol (100 ml) was added to dissolve the oil. Thin layer chromatography (tlc)(silica H. 2 0% methanol in chloroform) gave a $R_f$ much higher than the starting acetanilide.

Sodium bicarbonate (64 g, 0.6 Mol) was then added with stirring, followed by acetic anhydride (2 0 ml, 0.2 Mol) dropwise. Tlc (silica H. 3 0% ethylacetate in toluene) showed almost single spot $R_f$ of 0.3. The solution was stirred for 2 days, after which the tic showed that a change to a lower spot $R_f$ of 0.2 had occurred. The suspension was diluted with water (5 0 ml) and the product recovered by filtration and dried (9.1 g). The product was then washed twice with 5 0 ml ether to remove impurities (6.7 g, 56).

1c) N-ethyl-N4-nitrophenylethyl-3-hydroxyaniline
(V)

6 g of the N-2(4-nitrophenyl)ethyl-N-(3-hydroxyphenyl) acetamide prepared in 1b) was treated with borane in THF as in 1b). After removal of the THF, water was added and the product was recovered by filtration, washed with aqueous methanol and dried to give a product having the formula (V) (5.7 g, 80%).

Scheme 2

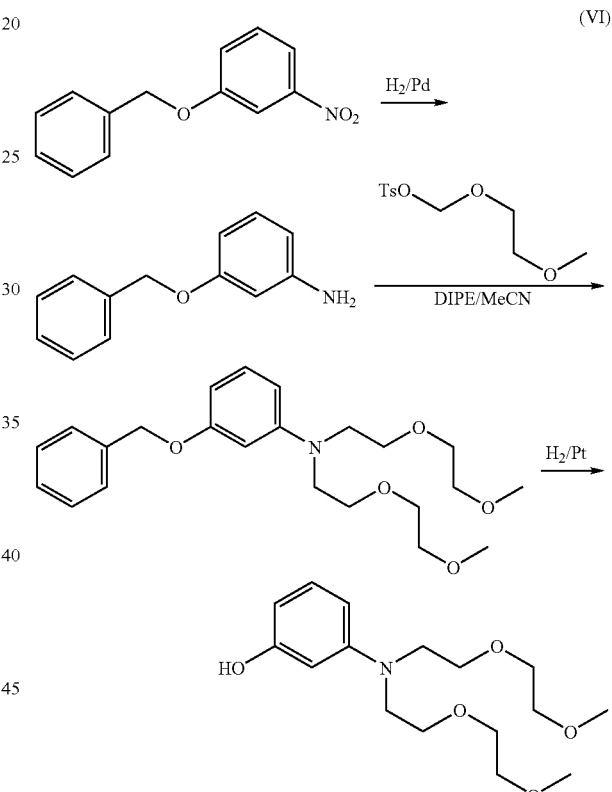

1d) Benzyl-3-nitrohenyl-ether

3-Nitrophenol (13.9 g) in DMF (30 ml) was treated with sodium carbonate (11 g) and benzybromide (17 g) under reflux. When the yellow colour of the reaction mixture had faded, 30% more carbonate and benzyl bromide was added under reflux. When only a slight pale yellow remained, analysis by tic confirmed the reaction to be complete. The product mixture was cooled; diluted with water (200 ml); extracted in toluene:petroleum (60-80)(1:1, 200 ml); washed with water (200 ml); dried with MgSOg; and evaporated. The product was crystallized from methanol (20 g, 87%).

Toluenesulphonyl chloride was added to 30% excess of methoxyethoxyethanol in pyridine and stirred overnight. 2 volumes of water was added, and the product recovered by filtration and dried.

1e) (3-Benzyloxy-phenyl)-bis-[2(2-methoxy-ethoxy)-ethyl-amine

Benzyl-3-aminophenyl ether (2 g) and 2-(2-methoxy-ethoxy)-ethyl p-toluenesulphonate (5.6 g) were heated under reflux in acetonitrile (5 ml) and diisopropylethylamine (4 ml) overnight. The reaction mixture was cooled and extracted into toluene, and the toluene was then washed with saturated sodium bicarbonate, dried and evaporated. Flash chromatography (gradient of toluene to 75% ethyl acetate in toluene over silica 60 (100 ml)) yielded some of the mono alkyl (0.25 g) and the required dialkyl amine (1.8 g, 44%).

1f) 3-{Bis-[2-(2-methoxY-ethoxy)-ethyl]-amino}-phenol (VI)

Benzyl-3-aminophenylether (1.8 g) was treated with 10% Pt/C (3 00 mg) in ethanol (3 0 ml) with acetic acid (5 ml). Hydrogen uptake was complete in 1 hour, and tic (silica 60, 10% methanol in chloroform) showed a single spot having a lower $R_f$ than the starting benzylether (silica 60). The catalyst was removed by filtration, the solvent evaporated and the product dried in vacuo (1.4 g)

Example 2

Condensation to Form a Mixture of Dyes

Compound (V) (1 g, 3.4 mMol), compound (VI) (2 g, 6.4 mMol), 5-nitrosalicylate methyl ester (0.5 g, 2.5 mMol) and silica gel 6 0 (4 g) were mixed and heated at 180° C. for 1 hour. The black powder obtained was cooled, more silica (10 g) was added and the mixture washed on a filter with ethyl acetate. The residue was extracted with acetic acid:chloroform: methanol (1:5:5), and the dark purple solution evaporated to dryness (1.6 g). Analysis by tic (dichloromethane: acetone: acetic acid, 60:30:10) showed three main purple bands, all slightly fluorescent when dipped in aqueous acetic acid, and all more fluorescent in dilute HCl. Column chromatography was performed on silica 60 (2 00 ml) eluting with 10% acetic acid in chloroform with a polarity gradient rising to 10% acetic acid in chloroform:acetone (1:2). After an initial brown material and a small purple band (including dye A) had been elated, fractions were collected. Those bands showing single components in the dichloromethane: acetone:acetic acid tic were evaporated to dryness to give highest $R_f$ (dyes B1 and B2, M+1 875.5, 45 mg), middle $R_f$ (dyes C1 and C2, M+1 903.5, 80 mg) and lowest $R_f$ (dye D, M+1 930.5, 30 mg) fractions.

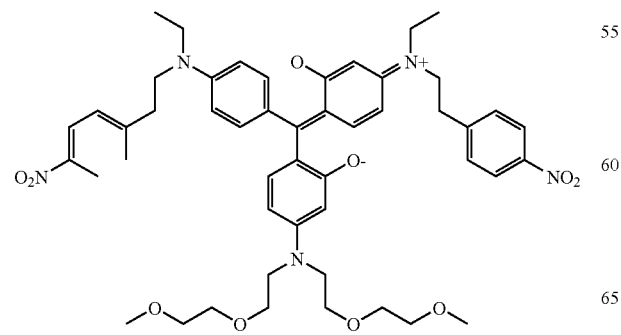

B1

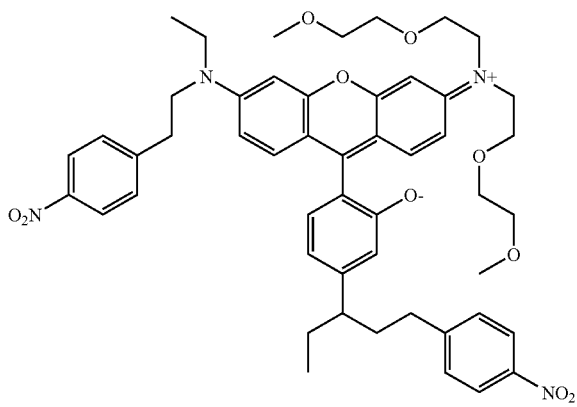

B2

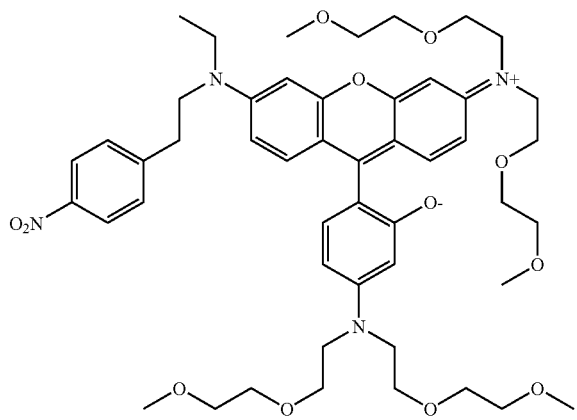

C1

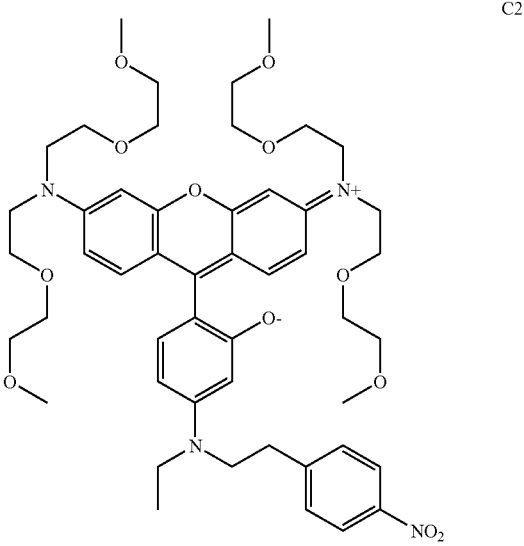

C2

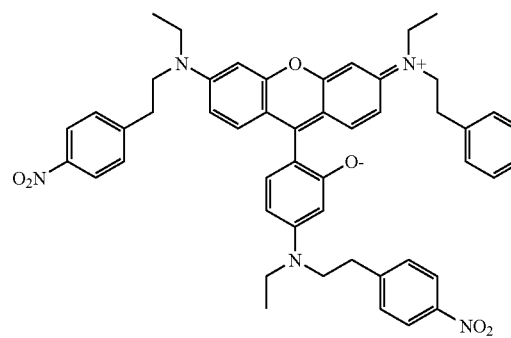

A

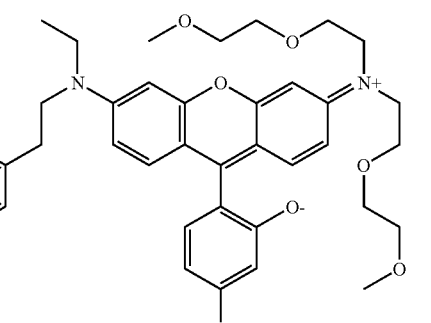

C1 amine
pKa 2.1

D

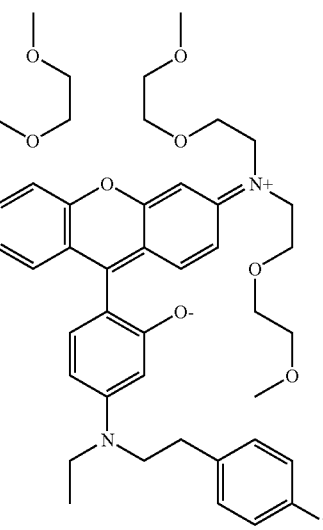

C2 amine
pKa 2.8

Example 3

Reduction and Separation of Dyes C1 and C2 Having Low pK$_a$'s and Conversion to Isothiocyanates 10 mg of the purified material of intermediate R$_f$ obtained in 2) above (i.e. a mixture of dyes C1 and C2) was dissolved in methanol (2 ml) and acetic acid (200 μl), treated with stannous chloride (100 mg) and stirred overnight. Tlc in dichloromethane (DCM):acetone:acetic acid (60:30:10) showed two spots with reduced R$_f$, both of which were strongly fluorescent when dipped in HCl. The reaction mixture was then diluted with HCl (0.1 M) and extracted with chloroform to give the higher R$_f$ material, i.e. the C1 amine shown below.

The reaction was repeated using 30 mg of a mixture of dyes C1 and C2 from 2) above, with extraction from dilute HCl and washing to give the C1 amine (8 mg), followed by neutralization with aqueous sodium acetate solution and extraction with chloroform and with methanol to give the C2 amine (15 mg).

For bonding to a target molecule, such as a protein, the amino group of the dye is converted to an isothiocyanate group by reaction with excess thiocarbonyldiimidazole in the minimum of chloroform. The isothiocyanate is precipitated by the addition of diethyl ether and the product isolated by centrifugation or filtration.

Example 4

Exchange Reaction to Increase pK$_a$ Followed by Reduction and Conversion to Isothiocyanate Two reactions were performed as follows:

4a) A mixture of dinitro dyes B1 and B2 (3 0 mg) was treated with diisopropylamine formate salt in DCM (1M, 1 ml) and diethylaminophenol (14 0 mg, 1 me).

4b) A mixture of mononitro dyes C1 and C2 (15 mg) was treated similarly.

The reactions were heated, with care to remove the DCM, and maintained at 150° C. for 1 hour. Each reaction gave rise to two main new products by tlc (silica H. DCM:acetone: acetic acid, 60:30:10), as shown below, with one product being common to both reactions and having an R$_f$ intermediate the starting material bands. This material was isolated by dissolving in chloroform, absorbing onto silica gel 60 (ca. g) and washing with chloroform. The purple dye products were eluted with chloroform:acetone:acetic acid (45:45:2 0) and evaporated to dryness. The residues were applied to two tic plates (silica H) and run in DCM:actone:acetic acid (60:40:10). The common band was removed and eluted with chloroform:methanol (1:1) and dried to give the exchange product from B2 and C1 (ca. 5 mg), which had a p$K_a$ of 4.2.

B1 ⟶

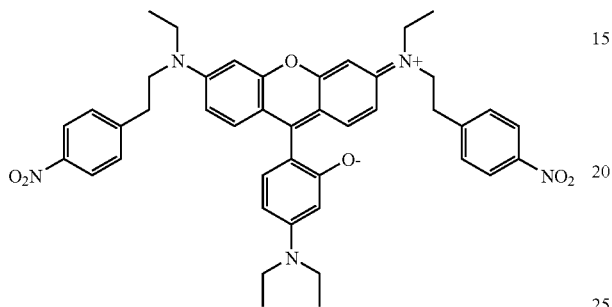

B2 and C1 ⟶

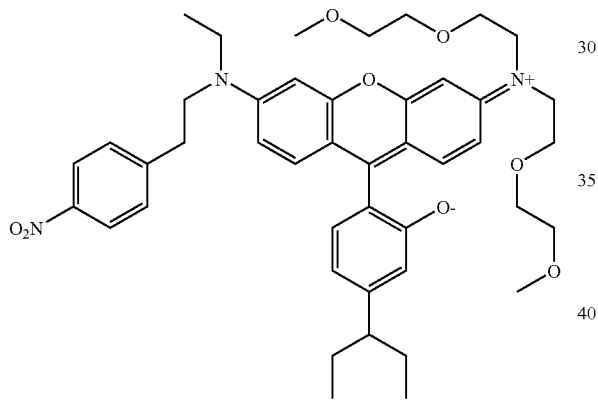

C2 and D ⟶

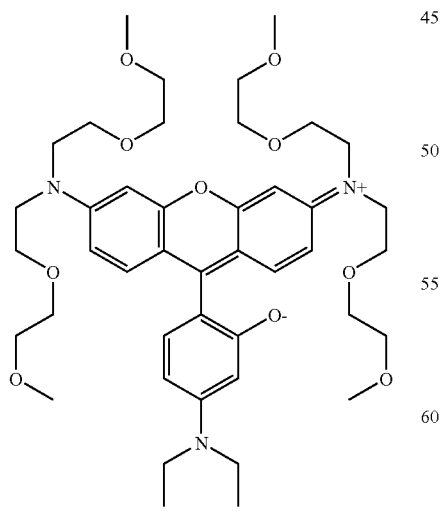

The reduction and conversion to the isothiocyanate was 2 8 performed as above.

Example 5

Labelling of Bovine Serum Albumin (BSA)

A dye having the formula (VII), below, has a fluorescence spectrum with an excitation maximum at 560 nm and an emission maximum at 585 nm, and a fluorescence titration as shown in FIG. 1.

The dye was dissolved in DMSO (10 mg/ml) and 10 μl of the resulting solution was added to a solution of defatted BSA (2 mg) in sodium carbonate buffer (50 μl, 100 mM, pH 8.5). The reaction was incubated at 35° C. for two hours. The solution was neutralized by the addition of acetic acid (1 M, 10 μl) and applied to a Sephadex G2 5 column (total bed volume 2 ml) and, equilibrated with triethylamine acetate buffer (25 mM, pH 6). The labelled protein was eluted in the exclusion volume (ca. 1 ml) and was collected and lyophilised.

(VII)

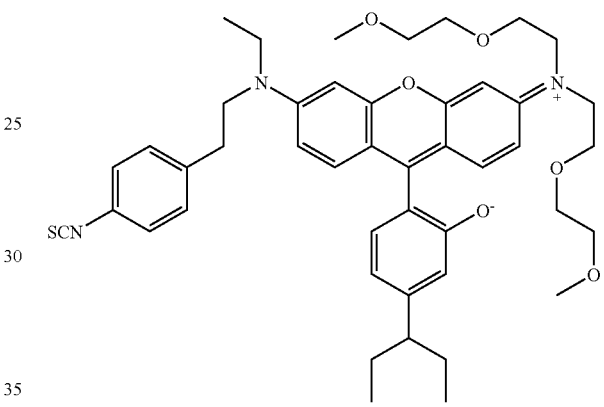

Example 6

Labelling of Aminodextran

A dye having the formula (VIII), below, was synthesized in a manner similar to that described in 2) above, but starting with commercially available 3-dimethylaminophenol in place of the di-methoxyethyoxyethylaminophenol (VI). This synthesis resulted in an isothiocyanate derivative with similar reporter properties but lacking sufficient solubility in aqueous media at neutral and higher pH, thereby precluding its use for protein labelling.

(VIII)

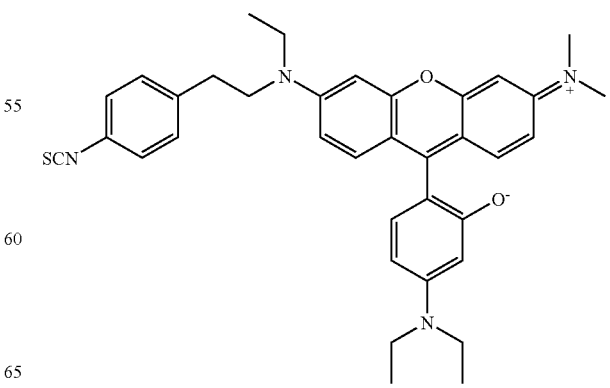

0.5 mg of compound (VIII) was dissolved in DMSO (10 μl) and added to T-10 aminodextran (supplied by Molecular Probes, Mr=10 kDa, 5 mg) dissolved in DMSO (50 μA) in a glass centrifuge tube. The solution was kept at room temperature for 1.5 hours and the labelling reaction was then halted with the addition of acidified ethanol (100 μl HCl, 12M, in 10 ml ethanol). The precipitated amino dextran was recovered by centrifugation (ca. 1000 G: 5 min) and the coloured supernatant solution was discarded. The precipitated pellet was then 3 0 redissolved in DMSO (ca. 1000) and acidified ethanol was added to precipitate and recover the aminodextran. The procedure was repeated three times until the supernatant was colourless. The washed, labelled aminodextran was dried under high vacuum (4.5 mg) then dissolved in a minimal volume of distilled $H_2O$ (<100 μl).

A sample of this solution was then applied to a 2 ml Sephadex G2 5 column that had been pre-washed with buffer solution (20 mM triethylamino-acetate in distilled water adjusted to pH 6.0 containing polyethylene glycol 400 (2% v/v)). A single coloured band passed through the column in the exclusion volume (ca. 1.0 ml). A small sample of the dried, labelled aminodextran was analysed by thin layer chromatography and no free dye was detected.

Example 7

Fluorescence-label LED Aminodextran is Endocytosed and Trafficked to Lysosomes (Internal Acidic)

This experiment was performed using NRK cells (a kidney cell line) that had been transfected with an over-expressing construct of a recombinant gene encoding a fusion protein between GFP (green fluorescent protein) and mucolipin. This construct ensures that the green fluorescence will be localised together with the mucolipin in the membrane of the lysosomes. The recombinant cells were incubated with the fluorescence-labelled aminodextran, produced in 6) above, at ca. 1 mg/ml for 1 hour and the medium was then replaced. At various time intervals thereafter the cells were inspected by confocal fluorescence microscopy at the wavelengths appropriate for detecting both GFP (green) and dye (VIII) of the present invention (red).

Figure 2:
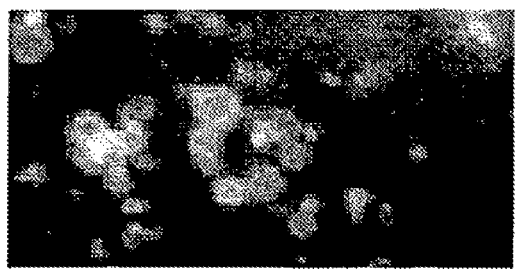
FIG. 2. High magnification confocal microscopic images of part of a single cell, showing lysosomes, taken after overnight incubation with the fluorescence-labelled aminodextran.
Figure 2:
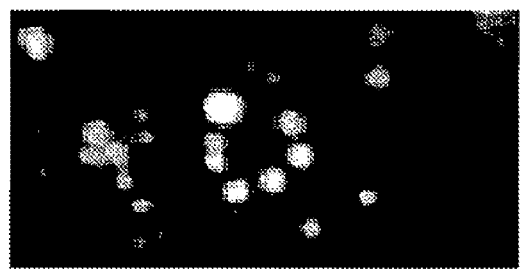
Figure 2:
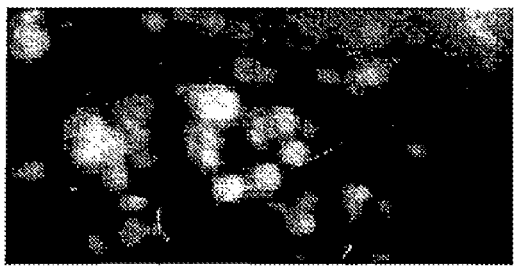
Figure 2:

FIG. 2 shows high magnification confocal microscopic images of part of a single cell, showing lysosomes, taken after overnight incubation with the fluorescence-labelled aminodextran.

The green fluorescence clearly shows GFP in the membrane of the vesicles. The red fluorescence shows fluorescence labelled aminodextran in an acidic environment (required for fluorescence of the dye VIII). The red fluorescence (luminal) appears only within lysosomes outlined by green fluorescence (membrane-bound). This result is accentuated in both the sum and difference images. Inspection of cells incubated with fluorescence-labelled aminodextran at earlier times showed little red fluorescence. However, all of the red fluorescence at early times was central to areas outlined with green fluorescence, as found at later times. This result also demonstrates the slow rate of traffic of aminodextran into the lysosomes. In addition, the presence of some GFP-labelled lysosomes not showing red fluorescence indicates that some lysosomes are not reached by aminodextran even after 20 hours of incubation.

Example 8

Preparation of 2-[3,6-bis-dimethylaminoxanth-9-ylium]-5-diethylaminophenol

Di-[3-dimethylaminophenyl]ether (12 mg, 0.05 mM) and 4-diethylaminosalicylaldehyde (9 mg, 0.05 mM) heated at 60° C. in HCl (100 μl, 2 M) for 1 day. Tlc (silica in chloroform: acetone:acetic acid 60:40:5) showed virtually all starting material gone, a small quantity of purple spot at $R_f$ 0.3 and a UV (254 nm) absorbing spot at $R_f$ approximately 0.6, which became bright purple on UV irradiation; this was 2[3,6-bis-dimethylaminoxanthen-9-yl]-5-diethylamino-phenol.

Two dimensional tlc in same solvent but with UV irradiation between elusions showed efficient conversion to the title compound. The reaction was diluted into ethanol and irradiated with UV at approximately 350 nm. The solution turned darker red and tic showed complete conversion of the colourless band into the lower $R_f$ purple band. The solution was neutralised with potassium carbonate (colour change red fluorescent to purple) and extracted into chloroform. The chloroform extract was purified by chromatography on two 20× silica G tic plates run in 20% methanol, 5% acetic acid in chloroform. Extraction of the purple band and evaporation gave the title compound (approximately 5 mg, 23%).

Example 9

9a) Preparation of 3-diethylamino-3'-dimethylamino-2,2'-dihydroxydiphenylmethanol

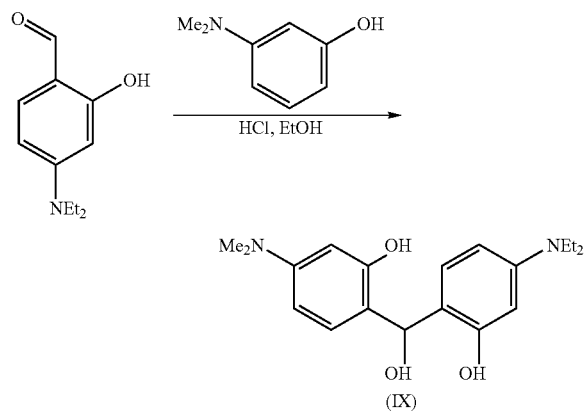

4-diethylaminosalicylaldehyde (193 mg, 1 mmole) and 3-dimethylaminophenol (170 me, 1.25 mmole) was dissolved in EtOH (10 ml) to which was added HCl (aq) (0.5 ml). The reaction was stirred at room temperature for 18 h. The solvent was removed in vacuo and the residue gasified. The product was extracted with $CHCl_3$, washed with $H_2O$, the organic layers were combined, dried and the solvent removed in vacuo to yield, the title compound, a light blue solid (264 mg, 80%).

9b) Preparation of 3-diethylamino-6-dimethylamino-9-hydroxyxanthene

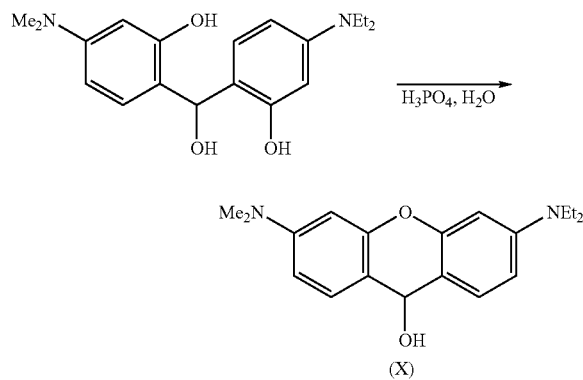

The acyclic methanol (IX) prepared in Example 9a (250 mg, 0.76 mmole) was dissolved in $H_2O$ (5 ml) to which was added two drops of $H_3PO_4$ (70%). The solution was heated under reflux for 2 h. The reaction was cooled and an excess of solid $Ba_2CO_3$ was added while stirring. The mixture was filtered and the solvent removed in vacuo to afford the hydroxy pyronin base (X) as a red solid (198.5 mg, 84%).

The pyronin base (X) may be converted to the corresponding I ketone (XI, below) using methodology described by Ehrlich et al, Chem. Ber. (1913) 46:1941.

9c) Preparation of 2-[3,6-bis-dimethylaminoxanth-9-ylium]-5-dimethylaminophenol

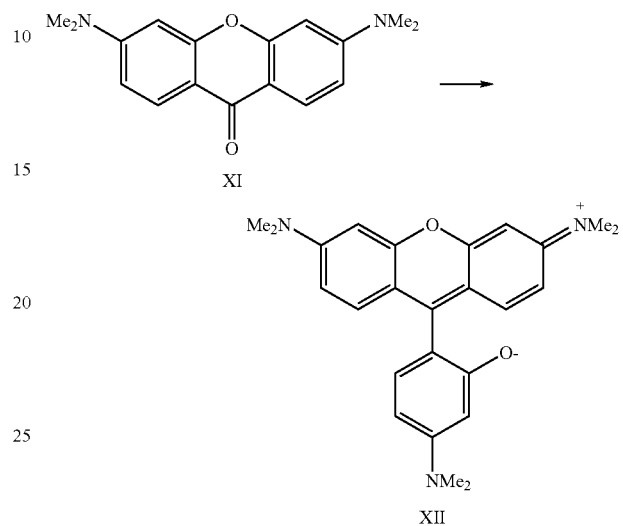

Commercial pyronin Y having the formula (XI) above (dye content usually approximately 50%) was extracted with hot ethanol, the solid impurities removed by filtration and the solvent evaporated.

The purified material (56 mg, 0.2 mM) dissolved in water was treated with potassium carbonate solution (0.2 ml, approximately 4M) and 5% Pt/C catalyst. The resulting suspension was stirred with EtOAc (5 ml) and treated with hydrogen peroxide (200 µl). When gas evolution finished the EtOAc layer was separated, and dried through a phase-separation filtration system and the solvent removed in vacuo to form (XI). The residue was dissolved in DCM and treated with dimethylaminophenol (28 mg, 0.2 mM) and the solvent removed by heating to 80° C. After 4 hours tlc (silica, chloroform:acetone: acetic acid, 60:40:5) showed complete conversion to the dye (XII). The dye was separated from the excess aminophenol by chromatography (silica, 2 0% methanol in chloroform) to give the title compound (20 mg, 70%).

Example 10

One pot preparation of 2-[3-diethylamino-6-dimethylamino-xanth-9-ylium]-5-dimethylaminophenol 4-Diethylaminosalicylaldehyde (19 mg, 0.1 mmole), 3 dimethylaminophenol (17 mg, 0. 13 mmole) were dissolved in $H_2O$ (5 ml) to which was added 3 drops of 70% H3PO4. The solution was stirred at 100° C. for 5 h. Tlc (silica, chloroform:acetone:acetic acid 60:40:5) showed loss of the two starting amines and appearance of a lower $R_f$ UV-absorbing compound identical to 3-diethylamino-6-dimethylamino-9-hydroxyxanthene. 3-Dimethylaminophenol (21 mg, 0.15 mmole) in 2M aqueous HCl (1 ml) was added and the reaction was stirred for a further 2 h. Tlc showed appearance of a spot with further reduced $R_f$. The solution was exposed to UV light to form the title compound derivative that ran on the same tlc at a much lower $R_f$, very close to that of, and with the same pH sensitivity as the closely related 2-[3,6-bisdimethylaminoxanth-9-ylium]-5-dimethylaminophenol.

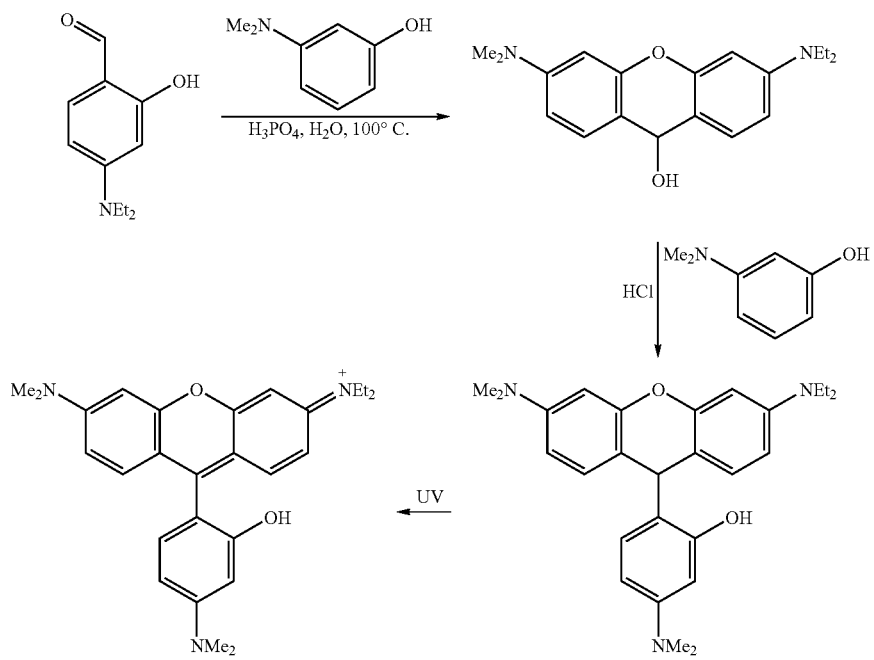

The invention claimed is:

1. A fluorescent dye comprising a xanthene-derived fluorophore having the formula (I)

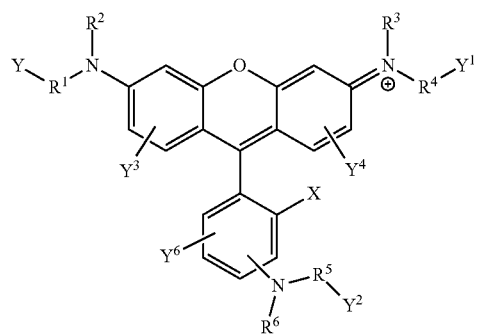

wherein $R^1$, $R^2$, $R^3$, $R^4$, $R^5$ and $R^6$ are independently selected from H, alkyl, alkoxy, alcohol, ether, alkenyl, alkenoxy, aryl, alkaryl, aralkyl and amido, except that $R^1$, $R^4$ and/or $R^5$ is not H when bonded to Y, $Y^1$ and/or $Y^2$ respectively;

X is either $O^-$ or $S^-$; and, at least one of Y, $Y^1$, $Y^2$, $Y^3$, $Y^4$ and $Y^5$ is a group for covalently bonding the dye, optionally through the use of a coupling agent, to a target molecule, and is otherwise H.

2. The dye of claim 1 wherein X is O.

3. The dye of claim 1 wherein the target molecule is selected from a peptide, a polypeptide, a protein, a saccharide, a polyeaccharide or an antibody.

4. The dye of claim 1 wherein the $NR^5R^6$ substituent is para to the xanthene moiety.

5. The dye of claim 1 which is water soluble.

6. A dye according to claim 5 wherein one or more of $R^1$, $R^2$, $R^3$, or $R^4$ is independently selected from alcohol, alkoxy and ether groups.

7. The dye of claim 1 wherein Y, $Y^1$, and/or $Y^2$ are selected from the group consisting of —NCS; —NCO; —(CO)R wherein R is a leaving group, H, OH, or alkyl; —SH; and, —$S_2$H.

8. The dye of claim 1 wherein at least one of Y and $Y^1$ is a group for covalently bonding the dye to a target molecule, and each of $Y^2$, $Y^3$, $Y^4$ and $Y^5$ is H.

9. The dye of claim 1 wherein $R^1$, $R^2$, $R^3$, $R^4$, $R^5$ and $R^6$ are alkyl groups and X is $O^-$.

10. The dye of claim 9 wherein each of $Y^2$, $Y^3$, $Y^4$ and $Y^5$ is H.

11. A method for making a dye of claim 1, comprising reacting a meta-aminophenol with a carboxylate compound capable of undergoing alpha-cleavage.

12. The method of claim 11 wherein a meta-aminophenol is reacted with the beta-ketocarboxylate diethylmalonate.

13. The method of claim 11 wherein a meta-aminophenol is reacted with 5-nitrosalicylic acid methyl ester.

14. A method for making a dye of claim 1 comprising reacting a compound having the formula (II)

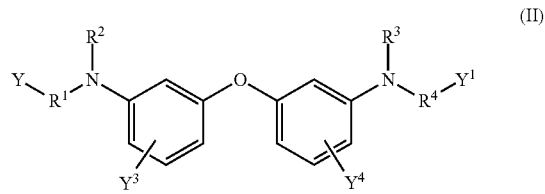

with a compound of formula $(CO)R^7_2$, wherein $R^7$ is a leaving group, to form an intermediate having the formula (III)

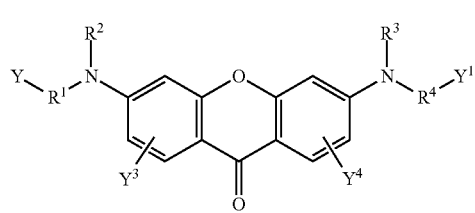

(III)

and converting the intermediate to a dye of claim 1.

15. A method for making a dye of claim 1, comprising reacting a compound having the formula (II):

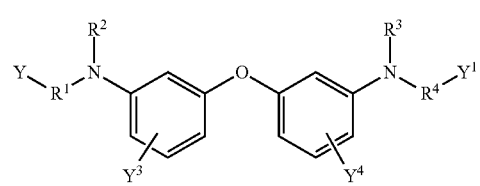

(II)

with a benzaldebyde, benzoic acid, activated benzoic acid or benzoate, wherein when reaction is with a benzaldehyde the resulting product is oxidized to form a dye of claim 1.

16. A method for making a dye of claim 1, comprising reacting together a pare-amino substituted salicylaldehyde and a meta-aminophenol to form a compound having the formula (IIa):

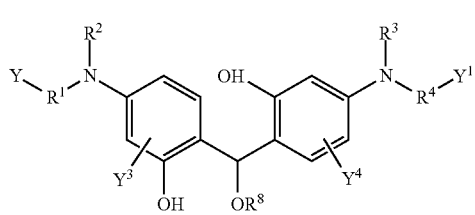

(IIa)

wherein $R^8$ is or an alkyl group;

cyclising the compound of formula (IIa) to form a compound having the formula (IIb):

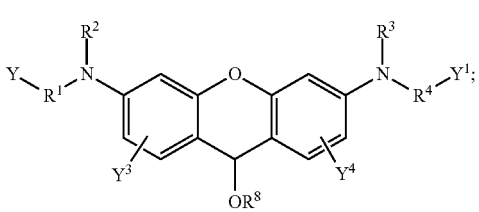

(IIb)

reacting the compound having the formula (IIb) with a meta-aminophenol to form a compound having the formula (IIc):

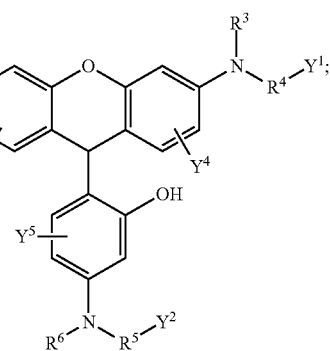

(IIc)

and, oxidising the compound having the formula (IIc) to form a dye of claim 1.

17. A method for making a dye of claim 1, comprising reacting together a para-amino substituted salicylaldehyde and a meta-aminophenol to form a compound having the formula (IIa):

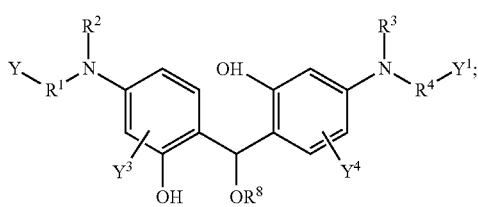

(IIa)

cyclising the compound having the formula (IIa) to form a compound having the formula (IIb):

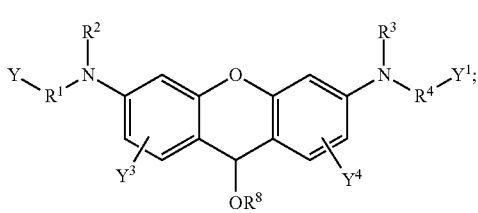

(IIb)

converting the compound having the formula (IIb) to a compound having the formula (III):

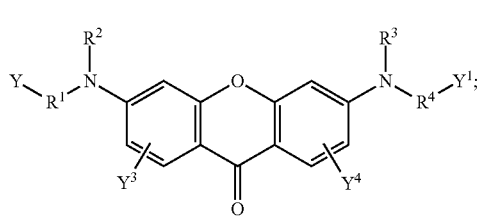

(III)

and, converting the compound having the formula (III) to a dye of claim 1.

18. A method for making a compound having the formula (IIb):

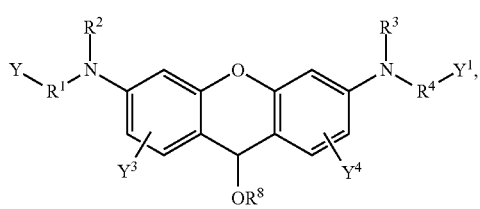

comprising reacting together a pare-amino substituted salicylaldehyde and a meta-aminophenol to form a compound having the formula (IIa):

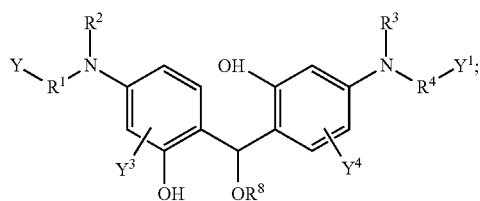

and cyclising the compound of formula (IIa) to form a compound having the formula (IIb).

19. A method of making a dye of claim 1, comprising reacting together a meta-aminophenol and a compound having the formula:

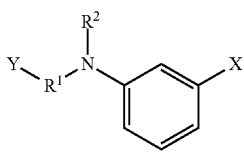

wherein X is a halogen, a B(OR$^9$)$_2$ group in which R$^9$ is H or an alkyl group or another leaving group, to form a compound having the formula (II):

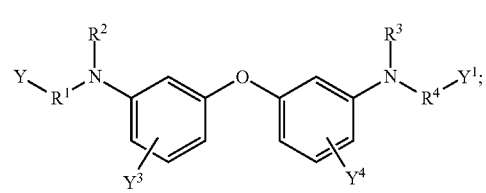

and, converting the compound having the formula (II) to a dye of claim 1 by a process selected from the group consisting of:

a) reaction with a salicylic ester;
b) reaction with a salicylaldehyde, and subsequent oxidation; and,
c) conversion to a compound having the formula (III)

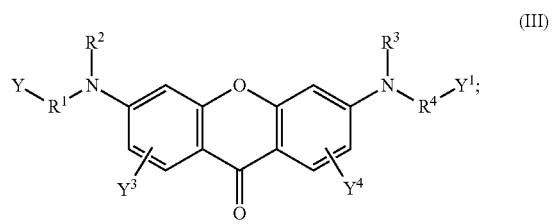

and, converting the product to a dye of claim 1.

20. A method of making a dye of claim 1, comprising functionalising a compound having the formula (IV):

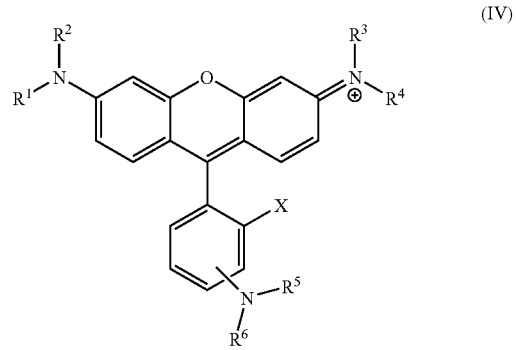

wherein R$^1$, R$^2$, R$^3$, R$^4$, R$^5$ and R$^6$ are independently selected from H, alkyl, alkoxy, alcohol, alkenyl, alkenoxy, aryl, alkaryl, aralkyl, amido and ether;

X is O or S; and, one or more of the aryl rings optionally includes an additional substituent, so as to incorporate at least one of Y, Y$^1$, Y$^2$, Y$^3$, Y$^4$ and Y$^5$ as a group for covalently bonding the dye, optionally through a coupling agent, to a target molecule.

21. A fluorescent complex comprising a dye of claim 1 bonded through Y, Y$^1$, Y$^2$, Y$^3$, Y$^4$ and Y$^5$ to a target molecule, optionally through a moiety derived from a coupling agent.

22. A complex according to claim 21, wherein the target molecule is selected from the group consisting of a peptide, a polypeptide, a protein, a saccharine, a polysaccharide, and an antibody.

23. A complex according to claim 21, wherein, in bonding to a target molecule, a linkage selected from —NH(CS)NH—; —NH(CO)—; —NHalkyl; —S(CS)NH—; —S(CO)—; and —SS, is created.

24. A living cell or cell compartment comprising a complex as defined in any of claims 21-23.

25. A method for determining the pH of a living cell or cell compartment comprising the steps of:
mixing a dye of claim 1 or a complex of claim 21 with a sample comprising a living cell or cell compartment;
allowing time for the dye or complex to enter the cell or cell compartment;
irradiating the cell or cell compartment;
measuring the intensity of fluorescence of the cell or cell compartment; and, determining the pH of the cell or cell compartment.

26. The method according to claim 25 which, in addition to said dye or complex, uses a second dye or complex having a different fluorescence response.

27. A method for analyzing the kinetics of migration into a cell or cell compartment of a dye of claim 1 or a complex of claim 21, the method comprising:
   mixing said dye or complex with a sample comprising a living cell or cell compartment;
   irradiating the cell or cell compartment for a time interval;
   monitoring the intensity of fluorescence of the dye or complex over the time interval; and,
   determining the time for migration of the dye or complex into the cell or cell compartment.

28. The method of claim 25 utilizing a plurality of different dyes or complexes, each of which has a different pKa, the method comprising:
   monitoring the intensity of fluorescence of each dye or complex over the time interval; and,
   determining the time for migration of each dye or complex into each cell or cell compartment.

29. The method of claim 28 utilizes a complex comprising a plurality of different dyes of claim 1 bonded to a target molecule, each dye having a different fluorescence response.

30. A pH testing kit comprising at least one dye of claim 1, or at least one complex of claim 21, and at least one set of calibration data.

* * * * *